United States Patent [19]

Stagg et al.

[11] 4,356,189

[45] Oct. 26, 1982

[54] CHEMICAL CASTRATION

[75] Inventors: Charles M. Stagg, St. Joseph; Ronald L. Tribble, Savannah, both of Mo.

[73] Assignee: Philips, Roxane, Inc., St. Joseph, Mo.

[21] Appl. No.: 235,326

[22] Filed: Feb. 17, 1981

Related U.S. Application Data

[63] Continuation of Ser. No. 29,637, Apr. 13, 1979, abandoned.

[51] Int. Cl.$^3$ ............................................. A61K 31/19
[52] U.S. Cl. ..................................................... 424/317
[58] Field of Search ........................................ 424/317

[56] References Cited

U.S. PATENT DOCUMENTS 4,156,427  5/1979  Fahim ............................. 424/145 X

OTHER PUBLICATIONS

Pineda et al. Am. J. Vet. Res., vol. 38, No. 6, pp. 831–838, 1977.
Bierschwal et al., Vet. Medicine, 1969, pp. 323–332.
Freeman et al.–Fertility & Sterility, vol. 24, No. 11, pp. 884–890, 1973.
Plant et al.–Australian Veterinary Journal, vol. 55, pp. 263–264, 1979.

*Primary Examiner*—Leonard Schenkman
*Attorney, Agent, or Firm*—Schmidt, Johnson, Hovey & Williams

[57] ABSTRACT

The invention is a unique procedure for chemical sterilization of male animals by injection of a suitable solution into both spermatic cords to cause sterilization with loss of libido and spermatogenesis. Chemical agents which have been found effective include weak acids and weak bases, lactic acid being preferred.

Secondly, the invention is a procedure for chemical sterilization of male animals by injecting lactic acid directly into both testis causing both loss of spermatogenesis and libido.

Thirdly, the invention is a procedure for chemical sterilization of male animals by injecting lactic acid into both caudel epididymis causing sterilization only.

10 Claims, No Drawings

CHEMICAL CASTRATION

This is a continuation of application Ser. No. 029,637, filed Apr. 13, 1979 and now abandoned.

This invention relates to a novel method for the sterilization of male animals and more particularly, relates to a method for chemical castration and chemical contraception of males which is simple, effective and has no undesirable side effects. The method by which chemical castration is accomplished is by injection of an appropriate composition into both spermatic cords or directly into both testes thereby causing atrophy of both testes. A method for chemical contraception without atrophy of testes is accomplished by injecting an appropriate composition into both caudel epididymis. These methods can be used on all kinds of male animals having external testes including domestic animals, farm animals, and exotic or zoo animals. More specifically, the methods comprise injecting aqueous lactic acid into the preferred site.

Many attempts have been made in the past to carry out successfully the sterilization of male animals by chemical means. A variety of chemical agents and mixtures both natural and synthetic have been studied and tested for their ability to render male animals unable to produce off-spring. Also, past efforts to effect such castrations have included various approaches to introducing the selected agents into the male reproductive organs. As examples, certain sclerotic agents have been injected into the caudel epididymis or vas deferens in order to interfere with the passage of live sperm from the testes to the exterior. Tests have also been carried out using various agents for injection into the testes themselves. These methods have been found to have a number of disadvantages such as lack of desired efficacy and/or failure to prevent libido and/or cause uncontrollable necrotic tissue damage.

It has long been possible to castrate male animals by surgical means. Surgical castration involves an open incision, which often results in infections, excessive bleeding, fly infestation and tetanus which can lead to death. Surgical procedures are well known to cause excessive stress in most animals and are never without pain.

The testes of the male animal perform two major functions. One is for spermatogenesis which originates in the seminiferous tubules, and the second is for the production of androgens (testosterone and dihydrotestosterone) which arise from the interstitual cells (Leydig cells). The sperm cells after their production within the testes are liberated into the head of the epididymis and travel to the tail of the epididymis. The tail of the epididymis (caudel epididymis) is made up of a cavernous network of convoluted tubules. The function of the epididymis is for transport, maturation, concentration, and storage of sperm. Upon ejaculation, sperm cells are liberated from the caudel epididymis into the vas deferens and eventually through the penis to the exterior. The function of both spermatic cords is to provide nutrient, gas exchange, and thermo-regulation for the testes by way of the pampiniform plexus vascular system.

It is a unique and essential feature of the invention that the agent be administered into both spermatic cords resulting in complete disruption of the vascular system thus causing testicular atrophy with loss of both spermatogenesis and libido.

Another feature of the invention is to inject lactic acid into both testes resulting in testes atrophy with loss of libido and spermatogenesis or inject into both caudel epididymis resulting in sterilization (contraception) without loss of libido.

The injecting substance which has been found to be most effective is a lactic acid solution. In any event, it is considered most effective to use an aqueous solution. Of particular usefulness is a lactic acid solution which should be U.S.P. grade or better. One such product is a mixture of lactic acid and lactic acid lactate which is equivalent to a total of not less than 85% and more than 90% by weight of lactic acid (U.S.P. grade).

Other materials which can be used for the injection method include acetic acid, acetic anhydride, propionic acid, butyric acid, succinic acid and the like. Lactic acid has been found to be dose related, which is a definite advantage over many other agents.

The chemical castration can be used for feline, canine, equine, bovine, ovine, and procine species of mammals. Specifically, the method is very successful and practical for bulls and male dogs. Injections made into boars, stallions, and male cats are less successful, primarily due to anatomical orientation and proportions of the male genitalia. Among mammalian species which could be successfully treated are those with pendulous type testis, such as male sheep and goats.

Among the limitations on the procedure are size and abnormal genitalia of the male to be chemically castrated. Thus, for more predictable and positive results, the treatment of the bull should be before his weight reaches about 500 pounds. With the dog, treatment of pups is not recommended.

The results of the procedure of the invention is atrophy of the testes by the preferred spermatic cord injections and secondly by intra-testis injections in small bulls causing ultimate loss of both libido and spermatogenesis; thirdly, injections of the caudel epididymis for chemical contraception without loss of libido.

Although it is necessary that veterinarians and others using the invention method have some procedural training, it has been found that a single demonstration or an explanation and/or an insert illustration are entirely adequate.

The invention procedure has been found to provide safe, rapid, economical and practical techniques for castration of animals. More rapid administration of the treatment is possible as compared to surgical castration. All the complications associated with surgical castration procedures are non-existent. Thus, it is safer, more humane, cleaner, and a great deal more convenient in every way than surgical castration.

It is also believed that this procedure of chemical castration may well yield greater performance results, that is for instance, showing increased feed efficiency and rate of weight gain in bulls. Generally, surgical castration has been found to set an animal back in growth at least two weeks. In connection with bulls, it becomes important to understand that chemically castrated bulls are, in reality and every way, steers and not bulls. With respect to bulls weighing in excess of 500 pounds, the situation is no different than for the emasculated or crimped animal. Thus, the larger chemically castrated bulls generally will be found to have non-functional testes remaining as their feeding time is too short to allow the testes to atrophy completely. In bulls weighing less than 500 pounds the animals will probably have no testes and at the time of slaughter, the scrotum will be shrunk.

The method has been shown to be versatile in its application and can be modified for various animals as required. For example, the volume and size of needle, as well as administration placement, can readily be modified for various animal species.

It is further to be noted, and the data obtained on animals has shown this, that lactic acid solution is preferred. It causes few side effects and is consistent in its effects. It is a normal, naturally occurring biological chemical and is therefore safe and predictable. It is, of course, also easy to assay in tissue samples and residues.

More specifically, in testing the chemical castration procedure, concentrations of lactic acid of from 5 to 85% in aqueous solution and from 0.25 to 16 mls. have been tested with success on bulls and male dogs and with limited success in stallions and boars.

The injection site of choice is both spermatic cords. The advantage of this site over intra-testes injections is that one needs only to cause damage to a relatively small area in contrast to the whole testis. However, in small calves (less than 100 lbs) the choice would be the testes injections as the testis is easier to inject and there is not much tissue at this size to destroy. The caudel epididymis injection procedure has the disadvantage of not eliminating libido; however, when a near intact male is desired, this may be the recommended choice such as for those male dog owners wanting a sterile masculine appearing dog and for those cattle owners desiring bulls for heat checking their cows without the risk of getting them bred to an unwanted male.

The invention technique developed for castration of male animals has wide application. This chemical castration has been employed for example, quite satisfactorily with bulls and male dogs. It has been found to be less useful for castration of male cats, pigs and stallions.

With respect to use of the method for bulls, there are approximately fifty to sixty million calves born in the United States each year of which approximately 50% are bull calves; there are potentially twenty to thirty million bull calves, most of which ordinarily undergo castration.

As for dogs, the method of the invention has great usefulness as a safe, rapid and economical method to produce male sterility as an aid in curbing the dog population. There is great need for an economical male sterilizing procedure in animal shelters and in areas where a differential dog license fee scale exists.

The first object of the experimentation was to determine the ease of administration of a chemical agent in several domestic male mammalian species. The use of Giemsa stain and lactic acid was used to determine both physical limitations and area of ensuing damage subsequent to administration. Three possible injection sites were explored, i.e., the spermatic cord, the testis, and the caudel epididymis.

It was found that a sound administrative approach for male dogs was both the caudel epididymis and spermatic cords and for bulls the spermatic cords and testes. It must be noted that caudel epididymis injections were not performed for the bull; however, this site of injection should be easy to administer the chemical agent.

It is very difficult to inject male cats and boars by either the caudel epididymis and spermatic cord approach due to the physical characteristics and orientation of the male genitalia. Administration approaches for rams have not been tested; however, no problems would be anticipated as their genitalia is of the same nature as for the bull.

It has been found that spermatic cord injections in the stallion presented no problem as to ease of administration; however, for reasons unexplainable at this time, the desired efficacy was lacking. Forty-nine injections were made into spermatic cords using various concentrations and volumes of lactic acid. Only nine successes were accomplished and these were not dose dependent.

The invention will be further described and defined by the following Examples, although it is in no way intended to limit the invention thereto.

EXAMPLE 1

A total of 173 bulls ranging in weight from 100 to 635 pounds were studied using both varying concentrations and varying volumes of lactic acid containing agent injected into both spermatic cords. An additional four bulls were emasculated to serve as positive controls. Thirty-seven of the 173 bulls injected weighed in excess of 500 pounds. The results of these studies are shown in Tables I and II below. Qualitatively, it was found that better results are obtained when the invention procedure is used on bulls weighing less than 500 pounds.

It was found that the lactic acid was dose-dependent on body weight. From the results in Tables I and II, it was found that the recommended dosage of 85% lactic acid for various weights is as follows:

| Minimum Effective Dosage (ml) | Body Weight Range (lbs.) | Percent Efficacy |
|---|---|---|
| 2 | 200 or less | 93 |
| 4 | 200 to 300 | 100 |
| 8 | 300 to 500 | 82 |

TABLE I

| | | | | | Individual Bull Efficacy Results | | | | |
|---|---|---|---|---|---|---|---|---|---|
| | | | | | Post-Treatment Results | | | | |
| L.A. Treatment | | | Initial Body | Left Side | | Right Side | | Blood Serum Levels of Testosterone (mh/ml) | | |
| Conc. (%) | Vol. (cc) | Bull No. | Weight (lbs.) | Day of Removal | Success (Yes or No) | Day of Removal | Success (Yes or No) | Initial | Day 13 | Final |
| Controls Emasculated (Crimped) | | 1 | 405 | 78 | Yes | 78 | Yes | — | — | — |
| | | 2 | 525 | 110 | Yes | 110 | Yes | 2.955 | — | 0.047 |
| | | 3 | 625 | 110 | Yes | 110 | Yes | 0.794 | — | 0.222 |
| | | 4 | 727 | 110 | Yes | 110 | Yes | 1.801 | — | 0.045 |
| 5 | 1 | 5 | 160 | 13 | No | 78 | No | 0.172 | 0.275 | 0.381 |
| | | 6 | 270 | 13 | Yes | 78 | No | 0.383 | 5.382 | 4.823 |
| | | 7 | 290 | 13 | No | 78 | No | 2.645 | 2.127 | 2.610 |
| | | 8 | 335 | 13 | No | 78 | No | 0.284 | 0.192 | 3.655 |
| | | 9 | 395 | 13 | No | 78 | No | 0.290 | 0.500 | 5.100 |
| | | 10 | 400 | 13 | No | 78 | No | 2.709 | 3.103 | 4.390 |

TABLE I-continued

Individual Bull Efficacy Results

| L.A. Treatment Conc. (%) | Vol. (cc) | Bull No. | Initial Body Weight (lbs.) | Post-Treatment Results | | | | Blood Serum Levels of Testosterone (mh/ml) | | |
|---|---|---|---|---|---|---|---|---|---|---|
| | | | | Left Side | | Right Side | | | | |
| | | | | Day of Removal | Success (Yes or No) | Day of Removal | Success (Yes or No) | Initial | Day 13 | Final |
| | | 11 | 425 | 13 | Yes | 78 | Yes | 0.013 | 0.089 | 0.063 |
| | | 12 | 490 | 13 | No | 78 | No | 0.680 | 1.780 | 1.773 |
| | | 13 | 635 | 13 | No | 78 | No | 4.860 | 1.480 | 1.374 |
| 10 | 1 | 14 | 175 | 13 | Yes | 78 | No | 0.524 | 0.631 | 0.724 |
| | | 15 | 205 | 13 | Yes | 78 | No | 0.453 | 1.045 | 3.146 |
| | | 16 | 240 | 13 | No | 78 | No | 4.536 | 3.560 | 2.950 |
| | | 17 | 310 | 13 | Yes | 78 | No | 0.196 | 0.377 | 0.368 |
| | | 18 | 410 | 13 | No | 78 | No | 0.301 | 0.148 | 1.525 |
| | | 19 | 410 | 13 | No | 78 | No | 0.510 | 3.360 | 0.672 |
| | | 20 | 415 | 13 | No | 78 | No | 2.060 | 0.084 | 0.748 |
| | | 21 | 468 | 13 | No | 78 | No | — | — | 7.937 |
| | | 22 | 525 | 13 | No | 78 | No | — | — | 8.585 |
| | | 23 | 525 | No Testis | | 78 | No | 1.350 | — | 0.280 |
| 20 | 1 | 24 | 255 | 13 | Yes | 78 | No | 0.144 | 0.091 | 0.935 |
| | | 25 | 310 | 13 | Yes | 78 | No | 1.720 | 1.457 | 2.469 |
| | | 26 | 400 | 13 | No | 78 | No | 9.340 | 6.350 | 0.785 |
| | | 27 | 418 | 13 | Yes | 78 | No | — | — | 7.927 |
| | | 28 | 420 | 13 | Yes | 78 | No | 4.418 | 0.280 | 2.261 |
| | | 29 | 420 | 13 | No | 78 | No | 0.370 | 0.650 | 5.240 |
| | | 30 | 460 | 13 | No | 78 | No | 0.380 | 0.590 | 0.348 |
| | | 31 | 485 | 13 | No | 78 | No | 3.550 | 3.270 | 2.944 |
| | | 32 | 506 | 13 | Yes | 78 | No | — | — | 6.017 |
| 20 | 2 | 33 | 330 | 13 | No | 78 | No | 1.481 | 3.212 | 5.179 |
| | | 34 | 400 | 13 | No | 78 | No | 7.734 | 1.136 | 0.540 |
| | | 35 | 450 | 13 | Yes | 78 | Yes | 2.113 | 1.748 | 0.126 |
| | | 36 | 455 | 13 | No | 78 | No | 1.225 | 3.433 | 3.936 |
| | | 37 | 575 | 13 | Yes | 78 | No | 2.484 | 8.495 | 3.106 |
| 40 | 1 | 38 | 100 | 84* | Yes | 84* | Yes | 0.202 | 0.070 | 0.070 |
| | | 39 | 135 | 119 | No | 119 | Yes | 0.097 | 0.204 | 0.204 |
| | | 40 | 155 | 112 | No | 112 | Yes | 0.525 | >6.000 | >6.000 |
| | | 41 | 175 | 13 | Yes | 78 | Yes | 0.013 | 0.047 | 0.084 |
| | | 42 | 180 | 13 | Yes | 78 | Yes | — | — | — |
| | | 43 | 270 | 13 | Yes | 78 | Yes | — | — | — |
| | | 44 | 415 | 13 | Yes | 78 | Yes | 9.597 | 2.072 | 0.360 |
| | | 45 | 435 | 13 | Yes | 78 | No | 3.260 | 0.050 | 2.409 |
| | | 46 | 440 | 13 | Yes | 78 | No | 3.920 | 0.640 | 0.360 |
| | | 47 | 455 | 13 | No | 78 | No | 0.490 | 0.345 | 0.776 |
| | | 48 | 500 | 13 | Yes | 78 | No | — | — | 2.336 |
| | | 49 | 508 | 13 | Yes | 78 | No | — | — | 5.141 |
| | | 50 | 525 | 13 | Yes | 78 | Yes | 9.420 | 0.360 | 0.321 |
| | | 51 | 535 | 13 | No | 78 | No | 1.193 | 0.726 | 1.247 |
| | | 52 | 565 | 13 | Yes | 78 | No | 8.070 | 0.840 | 0.321 |
| | | 53 | 600 | 13 | No | 78 | No | — | 9.260 | 9.047 |
| 40 | 2 | 54 | 115 | 46* | Yes | 46* | Yes | 0.562 | 0.085 | 0.085 |
| | | 55 | 116 | 133 | Yes | 133 | Yes | 0.072 | 0.062 | 0.062 |
| | | 56 | 143 | 71* | No | 71* | No | 0.040 | 0.088 | 0.088 |
| | | 57 | 150 | 133 | No | 133 | No | 0.314 | 0.141 | 0.141 |
| | | 58 | 150 | 119 | Yes | 119 | No | 0.561 | >6.000 | >6.000 |
| | | 59 | 170 | 133 | No | 133 | No | 0.458 | 0.452 | 0.452 |
| | | 60 | 187 | 133 | No | 133 | No | 0.117 | 0.629 | 0.629 |
| | | 61 | 195 | 119 | Yes | 119 | No | 0.442 | >6.000 | >6.000 |
| | | 62 | 290 | 133 | No | 133 | No | 0.505 | 0.994 | 0.994 |
| | | 63 | 295 | 133 | Yes | 133 | No | 4.991 | 0.868 | 0.868 |
| | | 64 | 310 | 133 | No | 133 | Yes | 6.702 | 0.394 | 2.394 |
| | | 65 | 335 | 133 | No | 133 | No | 0.370 | 0.850 | 0.850 |
| | | 66 | 415 | 13 | Yes | 78 | Yes | 8.084 | 0.046 | 0.108 |
| | | 67 | 425 | 110 | Yes | 110 | Yes | 0.136 | 0.112 | 0.112 |
| | | 68 | 500 | 110 | No | 110 | No | 6.439 | 10.707 | 10.707 |
| | | 69 | 570 | 13 | Yes | 78 | No | 0.922 | 7.428 | 1.219 |
| | | 70 | 570 | 13 | Yes | 78 | No | 0.292 | 0.348 | 0.815 |
| 40 | 4 | 71 | 351 | 124 | Yes | 124 | Yes | 0.194 | 0.076 | 0.076 |
| | | 72 | 371 | 124 | No | 124 | Yes | 8.348 | 0.586 | 0.586 |
| | | 73 | 401 | 124 | No | 124 | No | 0.256 | 0.411 | 0.411 |
| | | 74 | 447 | 124 | Yes | 124 | Yes | 0.217 | 0.078 | 0.078 |
| | | 75 | 447 | 18** | No | 18** | Yes | 2.241 | 4.023 | 4.023 |
| | | 76 | 463 | 124 | Yes | 124 | No | 0.314 | 0.765 | 0.765 |
| | | 77 | 481 | 110 | No | 110 | No | 2.043 | 6.663 | 6.663 |
| 40 | 8 | 78 | 466 | 110 | No | 110 | Yes | 3.442 | 1.951 | 1.951 |
| | | 79 | 476 | 124 | Yes | 124 | Yes | 0.367 | 0.111 | 0.111 |
| | | 80 | 502 | 124 | Yes | 124 | No | 0.612 | 0.789 | 0.789 |
| | | 81 | 527 | 124 | Yes | 124 | No | 0.829 | 1.582 | 1.582 |
| | | 82 | 595 | 124 | No | 124 | No | 8.961 | 0.765 | 0.765 |

TABLE I-continued

Individual Bull Efficacy Results

| L.A. Treatment Conc. (%) | Vol. (cc) | Bull No. | Initial Body Weight (lbs.) | Post-Treatment Results | | | | Blood Serum Levels of Testosterone (mh/ml) | | |
|---|---|---|---|---|---|---|---|---|---|---|
| | | | | Left Side | | Right Side | | | | |
| | | | | Day of Removal | Success (Yes or No) | Day of Removal | Success (Yes or No) | Initial | Day 13 | Final |
| | | 83 | 596 | 110 | No | 110 | No | 2.150 | 4.398 | 4.398 |

\* = Died from pneumonia
\*\* = Died from bloat

TABLE II

Individual Bull Efficacy Results

| Volume of 85% L.A. Injected | Bull No. | Initial Body Weight (lbs.) | Initial Blood Serum Testosterone Level (mg/ml) | Day | Post-Treatment Results: | | Final Blood Serum Testosterone Level (mg/ml) |
|---|---|---|---|---|---|---|---|
| | | | | | Success Rate (Yes or No) | | |
| | | | | | Left Testis | Right Testis | |
| 1 | 84 | 113 | 0.411 | 82 | Yes | Yes | 0.051 |
| | 85 | 116 | 0.642 | 82 | No | No | 1.040 |
| | 86 | 129 | 0.426 | 82 | No | Yes | 1.535 |
| | 87 | 157 | 0.465 | 82 | No | Yes | 0.476 |
| | 88 | 157 | 0.439 | 82 | No | Yes | 2.000+ |
| | 89 | 237 | 1.670 | 80 | No | No | 2.000+ |
| | 90 | 255 | 0.751 | 80 | No | No | 2.000+ |
| | 91 | 276 | 2.000+ | 80 | Yes | Yes | 0.157 |
| | 92 | 303 | 2.000+ | 80 | No | No | 1.626 |
| | 93 | 360 | 2.000+ | 80 | Yes | No | 2.000+ |
| 2 | 94 | 132 | 0.358 | 82 | Yes | Yes | 0.034 |
| | 95(a) | 139 | 0.080 | 73 | Yes | Yes | 0.111 |
| | 96(b) | 148 | 0.307 | 90 | No | Yes | 0.648 |
| | 97 | 169 | 0.651 | 104 | Yes | Yes | 0.038 |
| | 98 | 180 | 0.389 | 82 | Yes | Yes | 0.066 |
| | 99 | 182 | 0.570 | 90 | Yes | Yes | 0.044 |
| | 100 | 193 | 1.525 | 82 | Yes | Yes | 0.056 |
| | 101 | 201 | 0.628 | 104 | No | Yes | 0.528 |
| | 102 | 262 | 2.000+ | 80 | No | Yes | 2.000+ |
| | 103 | 272 | 2.000+ | 80 | No | No | 1.852 |
| | 104 | 331 | 2.000+ | 80 | No | Yes | 2.000+ |
| | 105 | 339 | 2.000+ | 82 | No | No | 2.000+ |
| | 106 | 443 | 5.001 | 110 | Yes | No | 13.504 |
| | 107 | 460 | 2.888 | 110 | Yes | No | 0.532 |
| | 108 | 483 | 1.746 | 110 | No | No | 16.765 |
| 4 | 109(a) | 146 | 0.069 | 60 | Yes | Yes | 0.127 |
| | 110 | 170 | 0.072 | 104 | No | Yes | 0.182 |
| | 111 | 200 | 0.143 | 104 | Yes | Yes | 0.136 |
| | 112 | 270 | 2.000+ | 87 | Yes | Yes | 0.176 |
| | 113 | 273 | 2.000+ | 97 | Yes | Yes | 0.052 |
| | 114 | 273 | 2.000+ | 97 | Yes | Yes | 0.062 |
| | 115 | 273 | 0.542 | 87 | Yes | Yes | 0.062 |
| | 116 | 297 | 2.000+ | 86 | Yes | Yes | 0.127 |
| | 117 | 305 | 1.730 | 100 | No | Yes | 2.000+ |
| | 118 | 328 | 0.233 | 99 | Yes | Yes | 0.105 |
| | 119 | 384 | 2.000+ | 87 | Yes | Yes | 0.043 |
| | 120 | 402 | 2.000+ | 107 | Yes | No | 2.000+ |
| | 121 | 429 | 0.693 | 108 | No | No | 0.641 |
| | 122 | 433 | 0.583 | 99 | Yes | Yes | 0.095 |
| | 123 | 438 | 0.585 | 107 | Yes | No | 2.000+ |
| | 124 | 441 | 0.472 | 107 | No | Yes | 2.000+ |
| | 125 | 445 | 0.270 | 99 | Yes | Yes | 0.055 |
| | 126 | 445 | 1.009 | 86 | No | No | 2.000+ |
| | 127 | 449 | 1.510 | 108 | No | Yes | 2.000+ |
| | 128 | 459 | 0.437 | 99 | Yes | Yes | 0.075 |
| | 129 | 471 | 0.590 | 99 | Yes | Yes | 0.093 |
| | 130 | 508 | 1.773 | 110 | No | No | 1.930 |
| | 131 | 510 | 0.437 | 110 | No | No | 0.361 |
| | 132 | 545 | 0.310 | 100 | No | No | 2.410 |
| | 133 | 625 | 0.583 | 100 | Yes | No | 0.612 |
| 8 | 134(a) | 140 | 0.047 | 21 | Yes | Yes | — |
| | 135 | 182 | 0.178 | 104 | Yes | Yes | 0.120 |
| | 136 | 223 | 0.866 | 104 | Yes | Yes | 0.115 |
| | 137 | 256 | 2.000+ | 56 | Yes | Yes | 0.069 |
| | 138 | 281 | 0.890 | 56 | Yes | Yes | 0.050 |
| | 139 | 290 | 0.570 | 56 | Yes | Yes | 0.049 |
| | 140 | 291 | 2.000+ | 56 | Yes | Yes | 0.049 |
| | 141(a) | 383 | 0.203 | 65 | Yes | Yes | — |
| | 142 | 399 | 2.000+ | 66 | Yes | Yes | 0.053 |
| | 143 | 403 | 0.680 | 77 | Yes | Yes | 0.214 |

TABLE II-continued
Individual Bull Efficacy Results

| Volume of 85% L.A. Injected | Bull No. | Initial Body Weight (lbs.) | Initial Blood Serum Testosterone Level (mg/ml) | Day | Success Rate (Yes or No) Left Testis | Success Rate (Yes or No) Right Testis | Final Blood Serum Testosterone Level (mg/ml) |
|---|---|---|---|---|---|---|---|
| | 144 | 424 | 2.000+ | 77 | Yes | Yes | >0.040 |
| | 145 | 427 | 0.640 | 77 | Yes | Yes | 0.198 |
| | 146(c) | 431 | 0.129 | 77 | No | No | 2.000+ |
| | 147 | 438 | 0.363 | 99 | Yes | Yes | 0.073 |
| | 148 | 458 | 0.414 | 99 | Yes | Yes | 0.058 |
| | 149 | 461 | 0.983 | 77 | Yes | Yes | 0.137 |
| | 150 | 471 | 0.347 | 99 | Yes | Yes | 0.088 |
| | 151(d) | 479 | 0.825 | 77 | No | No | 2.000+ |
| | 152 | 504 | 10.280 | 110 | Yes | No | 6.469 |
| | 153 | 506 | 0.771 | 107 | No | No | 2.000+ |
| | 154 | 543 | 0.418 | 108 | No | Yes | 0.778 |
| | 155 | 561 | 0.555 | 100 | Yes | Yes | 0.098 |
| | 156 | 563 | 0.356 | 100 | Yes | Yes | 0.044 |
| | 157 | 573 | 0.674 | 108 | No | No | 2.000+ |
| | 158 | 591 | 2.000+ | 107 | Yes | No | 2.000+ |
| | 159 | 600 | 0.504 | 110 | Yes | Yes | 0.040 |
| | 160 | 618 | 1.979 | 108 | No | No | 1.156 |
| 12 | 161 | 255 | — | 82 | Yes | Yes | 0.143 |
| | 162 | 261 | — | 82 | Yes | Yes | 0.056 |
| | 163 | 309 | 2.000+ | 86 | Yes | Yes | 0.068 |
| | 164 | 393 | 2.000+ | 107 | Yes | Yes | 0.036 |
| | 165 | 439 | 2.000+ | 108 | Yes | Yes | 0.149 |
| | 166 | 484 | 1.719 | 111 | Yes | Yes | 0.154 |
| | 167 | 536 | 0.853 | 108 | Yes | Yes | 0.180 |
| | 168 | 563 | 0.742 | 108 | No | Yes | 2.000+ |
| | 169 | 582 | 0.501 | 107 | No | No | 2.000+ |
| | 170 | 615 | 0.678 | 108 | Yes | Yes | 0.174 |
| | 171 | 619 | 2.000+ | 107 | Yes | Yes | 0.173 |
| 16 | 172(e) | 398 | — | 17 | Yes | Yes | — |
| | 173 | 426 | 2.277 | 111 | Yes | Yes | <0.038 |
| | 174 | 461 | 0.716 | 108 | Yes | Yes | 0.101 |
| | 175 | 558 | 1.109 | 107 | Yes | Yes | 0.210 |
| | 176 | 590 | 2.000+ | 107 | Yes | Yes | 0.202 |
| | 177 | 627 | 2.000+ | 108 | Yes | Yes | 0.159 |

(a) = Died from pneumonia
(b) = Extremely small genitalia to inject
(c) = Injected head of right epididymis; approximately ½ or right testis destroyed
(d) = Injected both heady of epididymis
(e) = Removed both testis due to severe ulceration on left side

EXAMPLE 2
Evaluation of High and Low Injection Sites

Twenty bulls had both spermatic cords injected with 8 c.c. of 85% lactic acid to test site of injection in spermatic cords. One side had the injection immediately above the testis and the other side was injected 1 to 1½ inches above the testis. The results of this study are shown in Table III below. Low injections proved superior to high injections, with an efficacy rate of 95% versus 80%, respectively.

EXAMPLE 3
Effectiveness for Baby Holstein Bulls

One and two c.c. of 85% lactic acid was injected directly into the testis of five small baby Holstein bulls. The experimental design and results are as follows:

| Bull No. | Days Old At Time of Infection | Vol. (c.c.) Injected Left | Vol. (c.c.) Injected Right | Efficacy Results Left Side | Efficacy Results Right Side |
|---|---|---|---|---|---|
| 178 | 0 | 1 | 2 | Yes | Yes |
| 179 | 33 | 1 | 2 | No | Yes |
| 180 | 7 | 1 | 2 | Yes | Yes |
| 181 | 7 | 1 | 2 | Yes | Yes |
| 182 | 1 | 1 | 2 | Yes | Yes |

It is evident from this study that lactic acid can be used for very young bulls calves, especially the first week or so following birth.

TABLE III
EVALUATION OF LOW AND HIGH INJECTION SITES IN TWENTY (20) BULLS

| Treatment Group | Bull Number | Initial Body Weight (Pounds) | Efficacy (Yes or No) Left Side | Efficacy (Yes or No) Right Side |
|---|---|---|---|---|
| | | | LOW | HIGH |
| A | 183 | 420 | Yes | Yes |
| | 184 | 375 | Yes | Yes |
| 8 c.c. of | 185 | 460 | Yes | No |
| 85% L.A. | 186 | 335 | Yes | Yes |
| | 187 | 390 | Yes | Yes |
| | 188 | 470 | Yes | Yes |
| | 189 | 405 | Yes | Yes |
| | 190 | 325 | Yes | Yes |
| | 191 | 485 | Yes | Yes |
| | 192 | 370 | No | No |
| | | | HIGH | LOW |
| B | 193 | 370 | No | Yes |

TABLE III-continued

EVALUATION OF LOW AND HIGH INJECTION SITES IN TWENTY (20) BULLS

| Treatment Group | Bull Number | Initial Body Weight (Pounds) | Efficacy (Yes or No) Left Side | Right Side |
|---|---|---|---|---|
| | 194 | 405 | Yes | Yes |
| 8 c.c. of | 195 | 360 | Yes | Yes |
| 85% L.A. | 196 | 435 | Yes | Yes |
| | 197 | 390 | Yes | Yes |
| | 198 | 380 | Yes | Yes |
| | 199 | 465 | Yes | Yes |
| | 200 | 375 | Yes | Yes |
| | 201 | 455 | Yes | Yes |
| | 202 | 485 | No | Yes |

EXAMPLE 4

Evaluation for Canine Sterilization

The use of lactic acid was studied as a possible chemical sterilant in the canine species. The results from injecting lactic acid into the caudel epididymis and spermatic cord are summarized in Tables IV and V, respectively.

The results shown in Table IV clearly demonstrate that 5 to 25% lactic acid functions as an effective chemical sterilant when injected directly into the caudel epididymis. The 85% lactic acid gave severe and prolonged ulceration.

The two control dogs identified as dogs Y and Z receiving surgical ligation of the pampiniform plexus show by comparison that interfering with the pampiniform plexus will sterilize a male dog.

TABLE IV

SUMMARY OF TISSUE DAMAGE RESULTING FROM INJECTING LACTIC ACID INTO THE CAUDEL EPIDIDYMIS OF THE CANINE
(Each Line Represents One Injection)

| Dog No. | % Lactic Acid in $H_2O$ | Volume Injected (c.c.) | Gauge × Inch Needle | Days Post-Injection Sacrificed | Tissue Damage Results To Caudel Epididymis (A) | Scrotal Ulceration (B) |
|---|---|---|---|---|---|---|
| X | Control - Ligated surgically both caudel epididymis; no sperm cells 4 days later | | | | | |
| 1 | 100 | 0.25 | 26 × ⅜ | 9 | ++ | ++ |
| 2 | 25 | 0.25 | 26 × ⅜ | 3 | ++ | 0 |
| 3 | 20 | 0.25 | 26 × ⅜ | 3 | ++ | 0 |
| 3 | 20 | 0.25 | 26 × ⅜ | 3 | ++ | 0 |
| 4 | 20 | 0.25 | 26 × ⅜ | 3 | + | 0 |
| 4 | 20 | 0.25 | 26 × ⅜ | 3 | + | 0 |
| 5 | 15 | 0.25 | 26 × ⅜ | 3 | ++ | 0 |
| 5 | 15 | 0.25 | 26 × ⅜ | 3 | ?* | 0 |
| 6 | 15 | 0.25 | 26 × ⅜ | 3 | ++ | 0 |
| 6 | 15 | 0.25 | 26 × ⅜ | 3 | ++ | 0 |
| 7 | 15 | 0.25 | 26 × ⅜ | 3 | ++ | 0 |
| 7 | 15 | 0.25 | 26 × ⅜ | 3 | ++ | 0 |
| 8 | 15 | 0.25 | 26 × ⅜ | 7 | ++ | 0 |
| 8 | 15 | 0.25 | 26 × ⅜ | 7 | ++ | ++ |
| 9 | 15 | 0.25 | 26 × ⅜ | 14 | ?* | 0 |
| 10 | 10 | 0.25 | 26 × ⅜ | 3 | ++ | 0 |
| 10 | 10 | 0.25 | 26 × ⅜ | 3 | ++ | 0 |
| 11 | 10 | 0.25 | 26 × ⅜ | 3 | ++ | 0 |
| 12 | 10 | 0.25 | 26 × ⅜ | 3 | ++ | 0 |
| 12 | 10 | 0.25 | 26 × ⅜ | 3 | + | 0 |
| 13 | 10 | 0.25 | 26 × ⅜ | 3 | + | 0 |
| 13 | 10 | 0.25 | 26 × ⅜ | 3 | + | 0 |
| 14 | 10 | 0.25 | 26 × ⅜ | 3 | 0 | 0 |
| 14 | 10 | 0.25 | 26 × ⅜ | 3 | + | 0 |
| 15 | 10 | 0.25 | 26 × ⅜ | 7 | ++ | 0 |
| 15 | 10 | 0.25 | 26 × ⅜ | 7 | ++ | 0 |
| 16 | 10 | 0.25 | 26 × ⅜ | 7 | ++ | 0 |
| 16 | 10 | 0.25 | 26 × ⅜ | 7 | ++ | + |
| 17 | 10 | 0.25 | 26 × ⅜ | 7 | ++ | 0 |
| 17 | 10 | 0.25 | 26 × ⅜ | 7 | ++ | 0 |
| 18 | 10 | 0.25 | 26 × ⅜ | 14 | ++ | 0 |
| 18 | 10 | 0.25 | 26 × ⅜ | 14 | ++ | 0 |
| 19 | 5 | 0.25 | 26 × ⅜ | 3 | ?* | 0 |
| 20 | 5 | 0.25 | 26 × ⅜ | 3 | + | 0 |
| 20 | 5 | 0.25 | 26 × ⅜ | 3 | ++ | 0 |
| 21 | 5 | 0.25 | 26 × ⅜ | 3 | ++ | 0 |
| 21 | 5 | 0.25 | 26 × ⅜ | 3 | ++ | 0 |
| 22 | 5 | 0.25 | 26 × ⅜ | 7 | + | 0 |
| 22 | 5 | 0.25 | 26 × ⅜ | 7 | + | 0 |
| 23 | 5 | 0.25 | 26 × ⅜ | 14 | + | 0 |

A - 0 = No observable damage
+ = Partially destroyed
++ = Completely destroyed
B - 0 = No ulceration
+ = Small ulceration
++ = Severe ulceration
*Difficult to determine influence of epididymis injection vs excess tissue damage resulting from spermatic cord injection Table V shows the results of injections of 25% to 10% lactic acid. These tests indicate that the percent efficacy for the 25%, 20%, 15%, and 10% lactic acid is 82% (14/17), 100% (6/6), 92% (12/13), and 80% (4/5), respectively.

TABLE V

SUMMARY OF TISSUE DAMAGE RESULTING FROM INJECTING LACTIC ACID INTO THE PAMPINIFORM PLEXUS OF THE SPERMATIC CORD OF THE CANINE
(Each Line Represents One Injection)

| Dog No. | % Lactic Acid in $H_2O$ | Volume Injected (c.c.) | Gauge × Inch Needle | Days Post-Injection Sacrificed | Tissue Damage Results Blood Circulation To Testis (A) | To P.P. (B) | To Head of Epididymis (C) | To Testis Proper (D) | Scrotal Ulceration (E) |
|---|---|---|---|---|---|---|---|---|---|
| Y | Control - Ligated both pampiniform plexus - no sperm cells 7 days later | | | | | | | | |
| Z | Control - Ligated both pampiniform plexus - no sperm cells 4 days later | | | | | | | | |
| 24 | 25 | 0.25 - Injected intra-testis - small area destroyed | | | | | | | |
| 25 | 25 | 0.5 | 27 × ⅜ | 3 | 0 | 0 | 0 | 0 | 0 |
| 25 | 25 | 0.5 | 27 × ⅜ | 3 | 0 | 0 | 0 | 0 | 0 |
| 26 | 25 | 0.5 | 26 × ⅜ | 3 | +++ | ++ | ++ | ++ | 0 |
| 27 | 25 | 0.5 | 26 × ⅜ | 3 | 0 | 0 | ++ | 0 | 0 |
| 27 | 25 | 0.5 | 26 × ⅜ | 3 | 0 | 0 | ++ | 0 | 0 |
| 28 | 25 | 0.5 | 26 × ⅜ | 7 | +++ | ++ | ++ | 0 | 0 |
| 28 | 25 | 0.5 | 26 × ⅜ | 7 | +++ | ++ | ++ | 0 | ++ |

TABLE V-continued

SUMMARY OF TISSUE DAMAGE RESULTING FROM INJECTING LACTIC ACID
INTO THE PAMPINIFORM PLEXUS OF THE SPERMATIC CORD OF THE CANINE
(Each Line Represents One Injection)

| Dog No. | % Lactic Acid in $H_2O$ | Volume Injected (c.c.) | Gauge × Inch Needle | Days Post-Injection Sacrificed | Blood Circulation To Testis (A) | To P.P. (B) | To Head of Epididymis (C) | To Testis Proper (D) | Scrotal Ulceration (E) |
|---|---|---|---|---|---|---|---|---|---|
| 29 | 25 | 0.5  | 26 × ⅜ | 7  | +++ | ++ | ++ | ++ | 0 |
| 29 | 25 | 0.5  | 26 × ⅜ | 7  | +++ | ++ | ++ | ++ | 0 |
| 30 | 25 | 0.5  | 26 × ⅜ | 7  | ++  | +  | ++ | 0  | + |
| 30 | 25 | 0.5  | 26 × ⅜ | 7  | ++  | +  | ++ | 0  | 0 |
| 31 | 25 | 0.5  | 26 × ⅜ | 7  | ++  | +  | ++ | 0  | 0 |
| 31 | 25 | 0.5  | 26 × ⅜ | 7  | ++  | +  | ++ | 0  | 0 |
| 32 | 25 | 0.5  | 26 × ⅜ | 14 | +++ | ++ | ++ | ++ | 0 |
| 33 | 25 | 0.25 | 27 × ¾ | 3  | ++  | +  | ++ | 0  | 0 |
| 33 | 25 | 0.25 | 27 × ¾ | 3  | ++  | +  | ++ | 0  | 0 |
| 34 | 25 | 0.25 | 26 × ⅜ | 3  | 0   | 0  | 0  | 0  | 0 |
| 34 | 25 | 0.25 | 26 × ⅜ | 3  | +++ | ++ | ++ | ++ | 0 |
| 35 | 20 | 0.5  | 27 × ¾ | 3  | ++  | 0  | 0  | 0  | 0 |
| 35 | 20 | 0.5  | 27 × ¾ | 3  | +++ | ++ | ++ | ++ | 0 |
| 36 | 20 | 0.5  | 26 × ⅜ | 3  | +++ | +  | +  | 0  | 0 |
| 36 | 20 | 0.5  | 26 × ⅜ | 3  | +++ | +  | +  | ++ | 0 |
| 37 | 20 | 0.25 | 26 × ⅜ | 3  | 0   | 0  | ++ | 0  | 0 |
| 37 | 20 | 0.25 | 26 × ⅜ | 3  | ++  | +  | ++ | 0  | 0 |
| 38 | 15 | 1.0  | 27 × ¾ | 3  | 0   | 0  | 0  | 0  | 0 |
| 38 | 15 | 1.0  | 27 × ¾ | 3  | +++ | ++ | 0  | 0  | 0 |
| 39 | 15 | 0.5  | 27 × ¾ | 3  | +++ | 0  | 0  | 0  | 0 |
| 39 | 15 | 0.5  | 27 × ¾ | 3  | +++ | 0  | 0  | 0  | 0 |
| 40 | 15 | 0.5  | 26 × ⅜ | 3  | +++ | ++ | +  | ++ | 0 |
| 40 | 15 | 0.5  | 26 × ⅜ | 3  | +++ | ++ | +  | ++ | 0 |
| 41 | 15 | 0.5  | 26 × ⅜ | 3  | +++ | ++ | +  | ++ | 0 |
| 41 | 15 | 0.5  | 26 × ⅜ | 3  | +   | 0  | ++ | 0  | 0 |
| 42 | 15 | 0.5  | 26 × ⅜ | 7  | +++ | ++ | ++ | ++ | 0 |
| 42 | 15 | 0.5  | 26 × ⅜ | 7  | +++ | ++ | ++ | ++ | 0 |
| 43 | 15 | 0.5  | 26 × ⅜ | 14 | +   | +  | ++ | 0  | 0 |
| 43 | 15 | 0.5  | 26 × ⅜ | 14 | ++  | +  | ++ | 0  | 0 |
| 44 | 15 | 0.5  | 26 × ⅜ | 14 | +++ | ++ | ++ | ++ | + |
| 45 | 10 | 0.5  | 26 × ⅜ | 3  | +++ | ++ | ++ | 0  | 0 |
| 45 | 10 | 0.5  | 26 × ⅜ | 3  | +++ | ++ | ++ | +  | 0 |
| 46 | 10 | 0.25 | 26 × ⅜ | 3  | ++  | +  | ++ | 0  | 0 |
| 46 | 10 | 0.25 | 26 × ⅜ | 3  | ++  | +  | 0  | 0  | 0 |
| 47 | 10 | 0.25 | 26 × ⅜ | 3  | 0   | 0  | 0  | 0  | 0 |

A - 0 = No effect on blood circulation to the testis
    + = Slight effect on blood circulation
  + + = Most of blood circulation is gone
+ + + = No blood circulation to testis
B - 0 = No observable tissue damage of pampiniform plexus (P.P.) and spermatic cord area
    + = Small area destroyed
  + + = Severe damage
C - 0 = No observable damage
    + = Partially destroyed
  + + = Completely destroyed
D - 0 = No observable damage
    + = Partial damage
  + + = Severe damage; incapable of producing sperm cells
E - 0 = No ulceration
    + = Small ulceration
  + + = Severe ulceration

What is claimed is:

1. A method of chemically castrating male mammals of the feline, canine, equine, bovine, ovine and porcine species of mammals comprising injecting into both testes or into both spermatic cords of said mammals a castratingly effective amount of lactic acid.

2. The method of claim 1 wherein the lactic acid is injected into both testes of the mammal.

3. The method of claim 1 wherein the lactic acid is injected into both spermatic cords and the mammal is a member of the bovine, canine, or ovine species.

4. The method of claim 1 wherein the mammal chemically castrated is a bull.

5. The method of claim 4 wherein an aqueous solution of lactic acid is employed.

6. The method of claim 5 wherein the lactic acid is injected into both testes of the bull.

7. The method of claim 5 wherein the lactic acid is injected into both spermatic cords of the bull.

8. The method of claim 5 wherein the bull weighs less than 500 pounds.

9. The method of claim 5 wherein an 85% concentration of lactic acid is employed.

10. The method of claim 1 wherein the mammal chemically castrated is a dog.

* * * * *